United States Patent
Alessi et al.

[11] Patent Number: 5,811,598
[45] Date of Patent: Sep. 22, 1998

[54] PROCESS FOR THE RECOVERY OF PHENOL FROM AN AQUEOUS STREAM CONTAINING NA$_2$SO$_4$

[75] Inventors: Vanni Alessi, Roncoferraro; Sabrina Astori, Mantova; Francesco Celin, Cerese di Virgilio; Cecilia Gradella, Cerlongo; Renzo Penzo, Mantova, all of Italy

[73] Assignee: Enichem S.p.A., Milan, Italy

[21] Appl. No.: 566,991

[22] Filed: Dec. 4, 1995

[30] Foreign Application Priority Data

Dec. 15, 1994 [IT] Italy .................................. MI94A2529

[51] Int. Cl.$^6$ ........................... C07C 37/72; C07C 37/74; B01D 11/04
[52] U.S. Cl. .............................. 568/754; 203/18; 203/46; 568/749; 568/798
[58] Field of Search .................................. 203/45, 18, 46, 203/71; 210/6, 34; 568/754, 749, 798, 706

[56] References Cited

U.S. PATENT DOCUMENTS

| | | |
|---|---|---|
| 3,963,610 | 6/1976 | Hauschulz et al. . |
| 4,026,791 | 5/1977 | Wallace . |
| 4,271,322 | 6/1981 | Matsunaga et al. ..................... 568/798 |
| 4,298,765 | 11/1981 | Cochran et al. ......................... 568/754 |
| 4,504,364 | 3/1985 | Chen et al. ............................... 203/46 |
| 4,559,110 | 12/1985 | Swearingen et al. ..................... 203/45 |
| 4,634,796 | 1/1987 | Suciu et al. .............................. 203/34 |
| 4,973,766 | 11/1990 | Penzo et al. ............................. 568/754 |
| 5,240,568 | 8/1993 | Chan et al. ............................... 203/84 |

FOREIGN PATENT DOCUMENTS 1 075 119  2/1960  Germany .

*Primary Examiner*—Virginia Manoharan
*Attorney, Agent, or Firm*—Oblon, Spivak, McClelland, Maier & Neustadt, P.C.

[57] ABSTRACT

Phenol dissolved in an aqueous sulphatic stream discharged from a reactor in which cumene hydroperoxide is oxidized to phenol and acetone is recovered by extracting phenol present in said aqueous sulphatic stream containing phenol, Na$_2$SO$_4$ and organic impurities, in a multi-step extractor with an organic solvent, thereby forming an extracted product organic phase and a refined aqueous product phase, the ratio of the extracted product phase to the refined product phase ranging from 0.1 to 1 v/v at a temperature ranging from 20°–70° C., and obtaining phenol by distillation or re-extraction of the recovered extracted product organic phase.

9 Claims, 3 Drawing Sheets

PROCESS FOR THE RECOVERY OF PHENOL FROM AN AQUEOUS STREAM CONTAINING NA₂SO₄

BACKGROUND OF THE INVENTION

1. Field of the Invention

The present invention relates to a process for the recovery of phenol from an aqueous stream containing $Na_2SO_4$.

2. Description of the Background

More specifically, it relates to a process for the recovery of phenol dissolved in an aqueous stream of a plant for the production of phenol from cumene, containing $Na_2SO_4$ and various organic impurities.

Phenol is prepared industrially by the oxidation of cumene and subsequent acid hydrolysis of the resulting cumene hydroperoxide. The reaction mixture obtained consists of phenol, acetone and non-reacted cumene.

In addition to the main products, various quantities of by-products are formed, such as for example, mesityl oxide, α-methylstyrene, p-cumylphenol, phenyl-dimethylcarbinol, acetophenone and phenols with a higher molecular weight.

The effluent from the scission reactors, which contains $H_2SO_4$ used as catalyst, is mixed with the aqueous streams containing sodium phenate coming from other sections of the plant and additional quantities of $H_2SO_4$.

The effluent is thus brought to a pH of about 7 which guarantees the salification of the sulphuric acid and organic acids formed as by-products during the reaction and, at the same time, releases the phenol from its sodium salt.

The mixture is then sent to a decanter to enable the separation of the organic phase containing phenol and other aromatic hydrocarbons from the aqueous phase containing $Na_2SO_4$ (7–15%) formed during the neutralization.

The organic phase is then sent to the primary distillation section, after washing with water, where the crude phenol is recovered and subsequently purified by distillation in a series of columns.

The aqueous phase which consists of "sulphatic" waters and varying quantities of phenol and acetone is discharged after recovering the latter.

Phenol and acetone are usually present in quantities within the range of 0.5–2 and 1.5–4% in weight respectively.

The recovery of the acetone is carried out by subsequent stripping whereas the phenol is usually recovered by counter-current extraction in a mixer-settler system. A stream of hydrocarbons mainly consisting of cumene, alpha-methylstyrene and acetone, taken from another section of the plant, is used as solvent.

The almost total recovery of the phenol (<100 ppm) is obtained by counter-current extraction in a system normally consisting of 2 mixer-settlers and with a very high quantity of solvent (the ratio solvent/refined product is about 3.5 v/v) to limit the number of steps necessary.

The phenol is then recovered from the solvent by extraction/salification with aqueous NaOH and the aqueous phenate solution is recycled to the neutralization section, whereas the solvent is continuously recycled to the extraction.

A simplified scheme of this type of extraction typical of the prior art, is shown in FIG. 1, in which cleft product from cumene hydroperoxide cleavage reactors is passed through line 1 into line 2 which is a recycle line from separating unit 12. An organic phase is discharged from separating unit 12 through line 3 by pump 4 from which phenol and acetone are recovered. An aqueous sodium phenate solution enters the separating unit 12 through line 5 as it is pumped by pump 6 through heat exchanger 7 into holding tank 8, and then the effluent from tank 8 passes by line 9 into tank 10. The contents of tank 10 are discharged through two lines 11 and 13 into separating unit 12. Sulphuric acid is added to the aqueous sodium phenate containing solution, passing through line 5, through line 14 to obtain phenol from its sodium salt; sodium sulfate being formed in this neutralization process.

Aqueous sulphatic process water containing some phenol and acetone is discharged from separating unit 12 through line 15 assisted by pump 16 into an extraction section. Extraction of the aqueous phase occurs in a first step by passing the aqueous phase and an organic stream from settler 26 through line 33 by centrifugal pump 20 through line 21 into settler tank 22. Aqueous sulphatic solution is withdrawn from settler 22 through line 27 by pump 28. The aqueous sulphatic solution from settler 22 is mixed with incoming organic solvent phase containing no phenol through line 31 in centrifugal pump 24, and then effluent from the pump is discharged through line 25 into settler 26. Aqueous sulphatic solution is withdrawn from settler 26 through line 29 by pump 30, and the aqueous sulphatic solution can then be further processed to remove acetone therefrom (not shown). Organic solvent phase is passed through settlers 26 and 22 by lines 31, 25, 33 and 21. Organic solvent phase containing phenol is withdrawn through line 35 from settler 22 and sent to the extraction/salification section of the process by way of line 37.

The extraction/salification section contains pumps 40, 42 and 44, settler 46 and separator 50. Organic solvent (37a), aqueous sodium phenate rich in NaOH from another section of the plant (37b), aqueous sodium phenate rich in NaOH from settler 46(line 38), and aqueous NaOH (37c) enter the section through line 37; the organic material containing phenol from settler 22 enters the section through lines 35 and 37. The mixture is efficiently mixed through centrifugal pump 42 and pumped into settler 46 through line 38. The organic solvent material, which now contains no phenol, is withdrawn from settler 46 through line 48 by pump 40 and divided into two streams. The first stream enters the extraction section through line 31. The second stream, having a flow rate equal to the amount fed to the system through line 37d, is washed with water fed through line 53, decanted in separator 50 and sent to be processed in the plant. The described water is recycled to the system through line 37d. Aqueous sodium phenate containing solution is withdrawn from the system and the extraction/salification section through line 52 by pump 44 and further processed in the plant. The aqueous sulphatic solution can then be further processed to remove acetone therefrom (not shown). Organic solvent phase is passed through settlers 26 and 22 by lines 31, 25, 33 and 21. Organic solvent phase containing phenol is withdrawn through line 35 from settler 22 and sent to the extraction/salification section of the process by way of line 37. The extraction/salification section contains pumps 40, 42, 44, settler 46 and separator 50. Organic solvent (37a), aqueous sodium phenate rich in NaOH from another section of the plant(37b) and aqueous NaOH (37c) enter the section through line 37; the organic material containing phenol from settler 22 enters the section through lines 35 and 37; aqueous sodium phenate rich in NaOH from settler 46 is recycled by pump 40. All these streams are efficiently mixed by the centrifugal pump 42, so that all the phenol is salified and passes into the aqueous solution, and sent to settler 46 through line 38. The organic solvent material, which now contains no phenol, is withdrawn from settler 46 through line 48 by pump 40 and divided into two streams. The main stream is recycled to the extraction section through line 31. The second stream, having a flow rate equal to the amount fed to the system through line 37*a*, is washed with water fed through line 53, decanted in separator 50, and sent to be processed into the plant. The decanted water is recycled to the system through line 37*d*. Aqueous sodium phenate solution still containing a large excess of NaOH is withdrawn from the system and the extraction/salification section through line 52 by pump 44 and further processed in the plant.

On the whole this system for the recovery of phenol from sulphatic waters represents a reasonable compromise between the necessity of keeping the investment cost of the equipment to a minimum and that of obtaining a reduction of the phenol of well below 100 ppm in the waters discharged.

There are however two negative aspects which should be taken into consideration:

the first of them is of an environmental nature and concerns the discharge, together with the waste water of the plant, of $Na_2SO_4$ which accompanies the recovery of the phenol from the solvent by extraction/salification with aqueous NaOH and subsequent neutralization with $H_2SO_4$.

the second is of an economic nature and relates to the cost of the NaOH and the equivalent stoichiometric quantity of $H_2SO_4$ necessary for the above recovery.

These drawbacks have been eliminated, or at least considerably reduced, in the process which represents the object of the present invention.

SUMMARY OF THE INVENTION

In its widest aspect, the invention relates to a process for the recovery of phenol dissolved in an aqueous stream of a plant for the production of phenol from cumene, containing $Na_2SO_4$ and various organic impurities which consists in the extraction of the phenol with a solvent from the aqueous stream and its subsequent recovery from the extracted product by distillation or re-extraction and is characterized in that the extraction of the phenol from the aqueous stream is carried out in a multistep extractor, using a ratio extracted product/refined product of between 0.1 and 1.0 v/v and at a temperature of between 20° C.–70° C.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
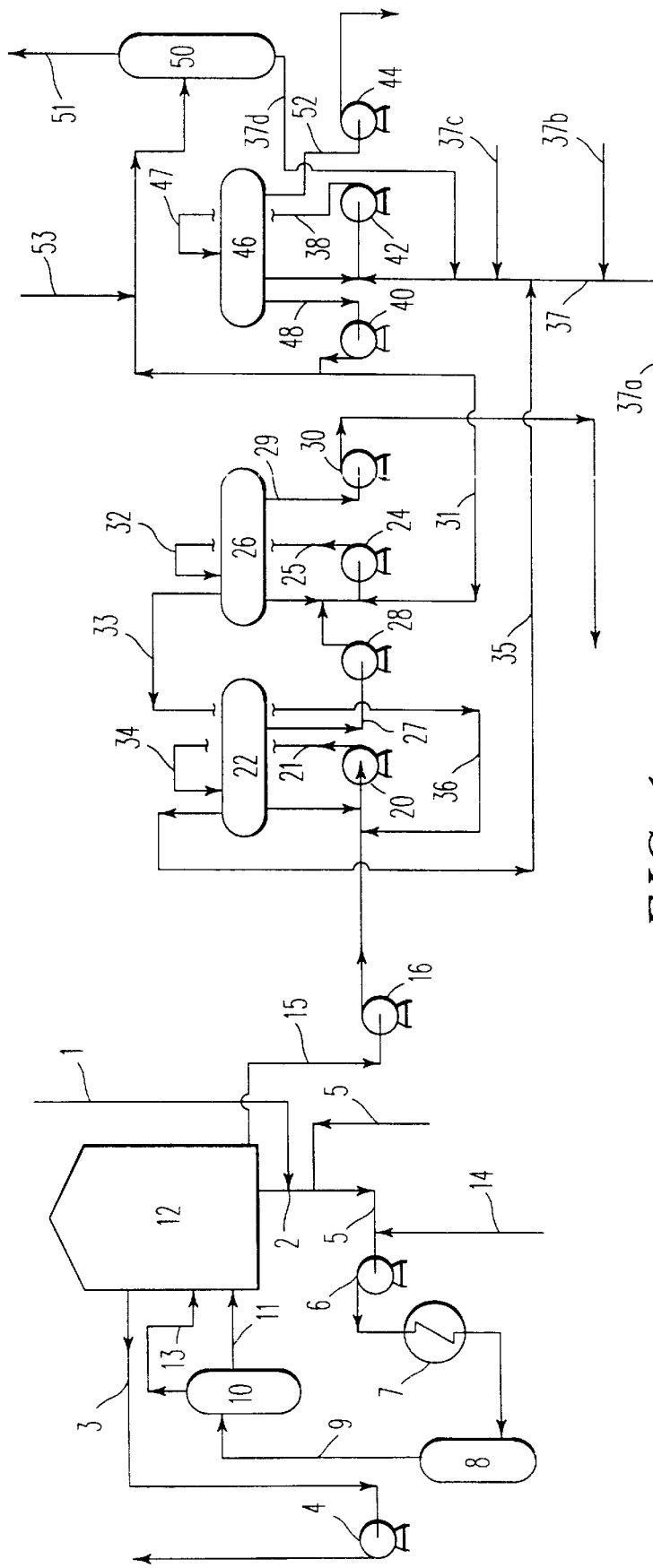
FIG. 1 is a process scheme of phenol extraction from sulphatic waters as practiced in the prior art.

The process of the present invention allows the production of an organic stream with a reduced flow rate, containing practically all the phenol which was previously dissolved in the sulphatic waters, which can be recovered in the distillation section of the plant or by re-extraction in a multistep extractor using, as solvent, an aqueous stream containing sodium phenate available in the plant, which is subsequently recycled to the neutralization section of the cracked product.

In this way, the recovery of phenol from water containing $Na_2SO_4$ avoids, either totally or partially, the consumption of NaOH and acid which occurs in the methods described in the known art.

The extraction of phenol with small quantities of solvent can be carried out by increasing the number of mixer-settlers or, even better, by using counter-current extraction columns (with perforated plates, with fillers, with stirring, pulsating etc.) which permits in a single extractor a number of extraction steps which can also be very high.

For the extraction, a filler-extractor was used, which can obviously be substituted by another multistep extractor of a different design.

For example, it is possible to use RDC, Kuhni, Scheibel, pulsating extractors, etc., provided that the number of extraction steps necessary for obtaining the desired reduction of the solute in the refined product is guaranteed.

Of crucial importance is the subsequent recovery operation of the phenol from the stream with a reduced flow rate obtained with this extraction which can be carried out by distillation or re-extraction.

In a plant for the production of phenol from cumene, the organic extract can be sent directly to the primary distillation section of the plant.

An accurate analysis of the problem has in fact shown that if the distillation conditions are suitably modified, such conditions normally used in processes for the production of phenol from cumene, can be used for the recovery of the phenol.

With reference, therefore, to our industrial process for the production of phenol, in the first column of the primary distillation section a stream consisting of acetone, water and all the aromatic hydrocarbons present in the cracked product is separated at the head, whereas the phenol and high-boiling products are obtained at the bottom of the column.

The main products for this separation are: phenol, which in the stream at the head must not exceed 0.5% w; and α-methylstyrene which in the stream at the bottom must not exceed 0.1% w.

The phenol present in the stream at the head of the column is subsequently recovered by salification with NaOH, whereas that remaining in the stream at the bottom is recovered by subsequent distillation in a series of columns which allows an initial separation of the high-boiling products and subsequent elimination of the impurities from the crude phenol.

As a result, the distillation conditions which enable the level of the phenol to be kept constant in the stream at the head even after adding to the cracked product the organic product coming from the extraction of phenol, in which the phenol is present in a concentration within the range of 2–20%, cause a considerable reduction in the consumption of soda and sulphuric acid.

These conditions are reached when the reflux ratio of the column is suitably modified.

The energy cost is greater but is much less than any saving which can be obtained by a lower consumption of NaOH.

This avoids consuming a considerable quantity of NaOH and acid which would otherwise be necessary using the methods described in the known art.

With a reflux ratio, for example, of about 0.3, a concentration of phenol in the hydrocarbon stream of about 0.5% w (Example 3 of Table 3) is obtained.

After adding the corresponding quantity of hydrocarbon stream coming from the extraction test and appropriately varying the reflux ratio, the phenol in the stream at the head is still 0.5% w (Example 4 and 5 of Table 3).

From a balance of the phenol present in the stream at the head before and after the addition of the hydrocarbon stream coming from the extraction, the possible saving of soda is evaluated.

In this case the saving obtained corresponds to about 95% of the phenol extracted from the aqueous di-sulphate solution.

A different primary distillation scheme for phenol plants is described in the Reports of the Stanford Research Institute (YEN-CHEN-YEN; report No.22B; S.R.I.—Mainlo Park, Calif.).

In the first column there is the separation of the acetone alone (together with traces of water); whereas the hydrocarbons, which pass with the phenol into the bottom of the first column and into the head of the next column which cuts the high-boiling products (C-304), are collected together with the water in the stream at the head of the cumene column (C-305) at whose bottom the crude phenol is separated.

Similarly to what is described above, also in our process the phenol present in the stream at the head is subsequently separated by salification with soda.

A comparison of the results we obtained with this conditions of the distillation section indicates that also in this case it is possible to recover about ¾ of the phenol from the bottom of the column (therefore without consumption of NaOH). (Example 6 and 7 of Table 3).

In other processes the conditions of the distillation section is similar to that described in the Stanford report but the feeding to the hydrocarbon column consists of the bottom product of a previous separation whereby not only the acetone but a part of the water is distilled, a situation of this kind is simulated in Example 8.

The addition of the organic stream coming from the extraction, to this feeding causes, with the same reflux, a limited increase in the phenol in the stream at the head, but also in this case the total balance of the soda consumption is favourable, as about 60% of the phenol is recovered without having to resort to salification.

Alternatively, the recovery of the phenol from the stream coming from the extraction can be carried out in another multistep extraction apparatus using as solvent an aqueous solution containing sodium phenate taken from another section of the plant.

In this case the recovery which is complete (99.9%; Example 10), takes place without the necessity of subsequent salification with soda and without any increase in energy consumption.

In the past, we studied a process of this kind for the recovery of phenol contained in an organic stream coming from purification columns of phenol (EP 372685). The addition to this stream of the solvent phase coming from the extraction of sulphatic waters, on the one hand causes an increase in the stream rate of the refined product, but on the other modifies the physico-chemical characteristics to such a degree that, on the whole, it is not necessary to increase the flow rate of the solvent.

Examples 1 and 2 illustrate a possible setting of operating conditions for the extraction and the results which can be obtained, without limiting the scope of the present invention.

Examples 3, 4 and 5, describe distillation tests carried out in the laboratory which simulate the conditions of the distillation section of our process; Examples 6 and 7 simulate the distillation section conditions indicated by Stanford; Examples 8 and 9 simulate a third possible condition for the separation of acetone, water and hydrocarbons from phenol and high-boiling products; Examples 10, 11 and 12 refer to the recovery tests by means of re-extraction.

EXAMPLE 1

For this extraction a jacketed extractor is used having an internal diameter of 75 mm and containing 0.5" Raschig carbon rings, for a total height of 10.5 m. The filling was sub-divided into three 3.5 m sections, each of which was supported by a wide mesh steel net over which was a perforated plate with suitably sized and shaped holes for the dispersion of the aqueous phase inside the filler below and for the discharge of the continuous phase from the lower section to the upper one.

Figure 2:
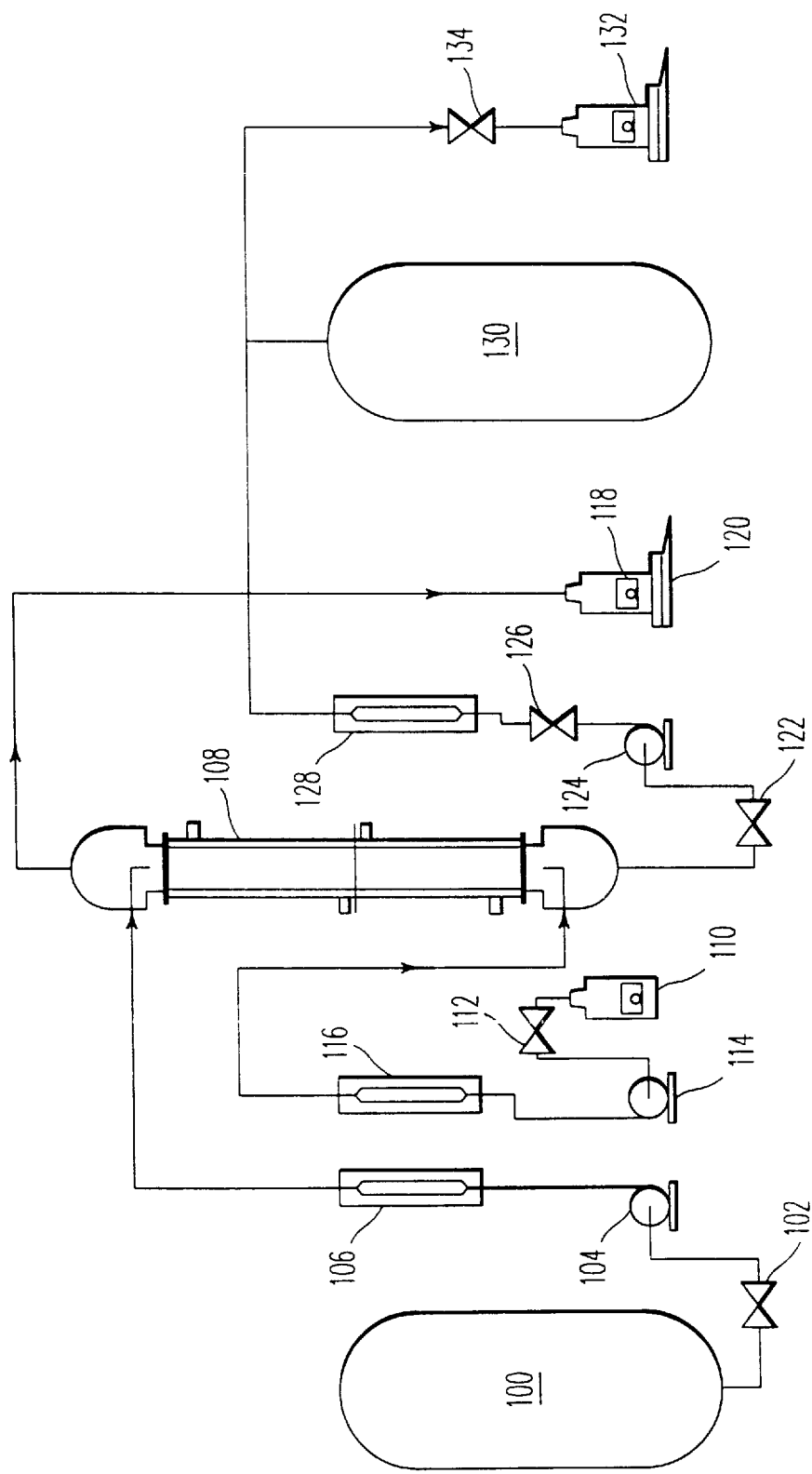
FIG. 2 shows the apparatus and process scheme of the present invention.

FIG. 2 shows the scheme of the apparatus in which tank 100 contains aqueous sulphatic solution. Valve 102 controls the flow of the aqueous sulphatic solution which is moved by pump 104 through rotameter 106, which controls the rate of flow of the aqueous sulphatic solution into extractor 108. Organic solvent solution in tank 110 flows through valve 112 by pump 114 and the rate of flow of organic solvent solution into extractor 108 is controlled by rotameter 116. Counter-current extraction occurs in the extractor 108 with organic solvent solution containing phenol exiting the extractor at its top and removed to outlet 118 on balance 120. Aqueous sulphatic solution is withdrawn from the extractor through valve 122 by pump 124 and then through valve 126 under control by rotameter 128. The outflowing aqueous phase flows to holding tank 130 and aqueous phase outlet 132 through valve 134.

The following products were fed to this column maintained at a temperature of 60° C. by temperate water: at the filling base 9.65 Kg/h of an organic solvent (103) mainly consisting of cumene and containing α-methylstyrene and acetone (it is known that the presence of acetone improves the equilibrium distribution when the phenol is extracted from an aqueous solution), taken from a section of the industrial plant for the production of phenol, and at the top 61.25 Kg/h of an aqueous solution of $Na_2SO_4$ (101) containing phenol, also taken from the industrial plant. During the passage through the column the phenol contained in the aqueous phase was extracted into the organic phase. The composition of the two feeding and discharge streams (aqueous 105 and organic 107) is shown in Table 1, FIG. 3.

EXAMPLE 2

Figure 3:
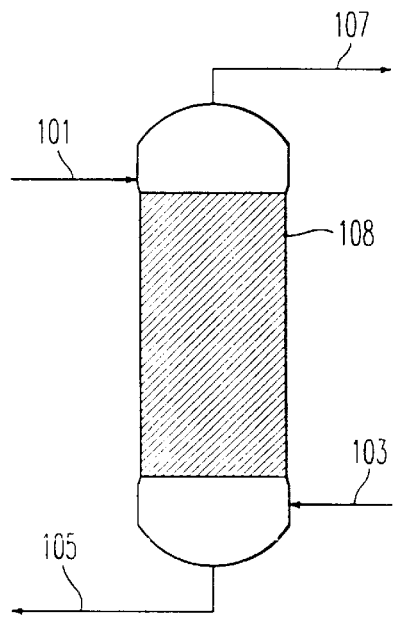
FIG. 3 shows the extraction unit of the present process with aqueous phase and organic phase feeds and outlet lines.
Figure 4:
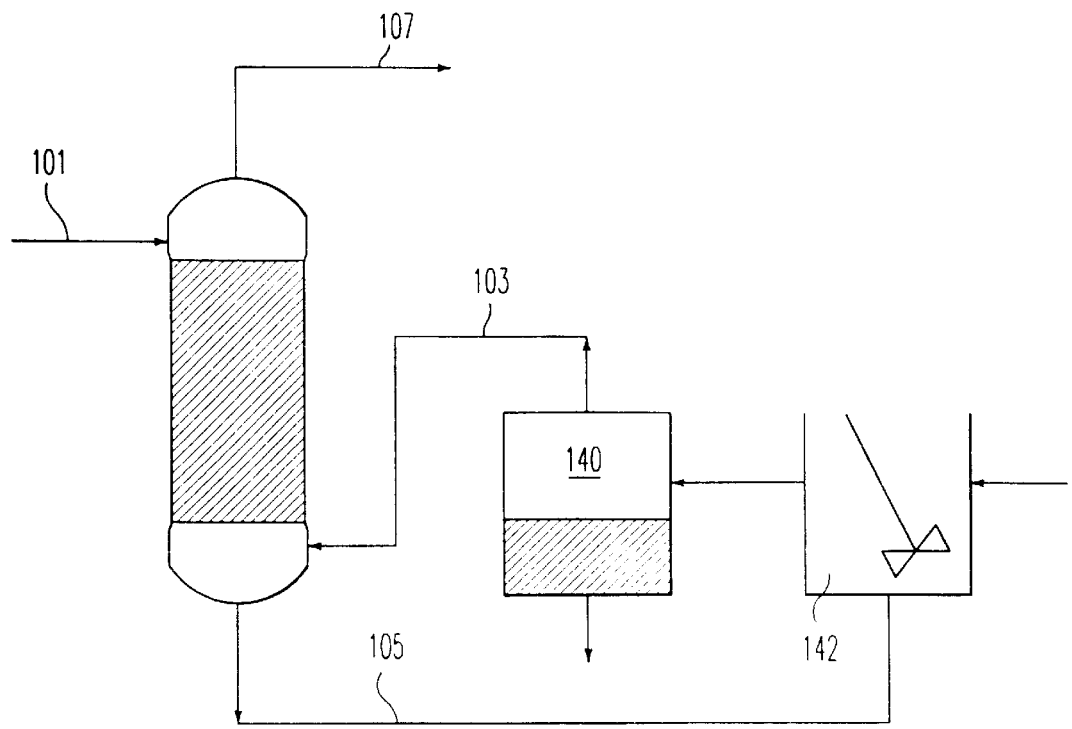
FIG. 4 shows an embodiment of the apparatus of FIG. 3 in which a mixer-settler is incorporated.

Not having obtained the desired reduction of the phenol in the refined effluent to values lower than 100 ppm, the apparatus of Example 1 as shown in FIG. 3 was modified adding a mixer(142)-settler(140), into which aqueous and organic material are fed, so that the refined effluent could be further extracted from the solvent, before this was fed to the extractor. Using the same streams and flow rates as Example 1, an extraction test was carried out which gave the results illustrated in Table 2 FIG. 4, from which it was observed that the residual phenol in the effluent organic phase was reduced to below 100 ppm.

EXAMPLE 3 (as a reference)

A sample of cracked product having the following % w composition was taken from the industrial plant: acetone 25.7; cumene+butylbenzenes 9.9; α-methylstyrene (α-MS) 2.4; phenol 46.5; high-boiling products 5.5; water 10.0. It was fed, at a flow rate of 400 g/hr, between plate 15 and 16 (numbering which starts from the top) of an Oldershaw glass distillation column consisting of two sections, each containing 25 1.1" plates and insulated by means of a Dewar jacket. The section above the feeding was suitable for the distillation of aqueous systems (50 holes per plate); the section below the feeding was suitable for the distillation of organic systems (80 holes per plate). 193 and 207 g/hr were removed from the head and bottom of the column respectively.

The test conditions and main results obtained are shown in Table 3.

EXAMPLE 4

4.23 parts by weight of the extract of Example 2 were added to 100 parts by weight of the sample of cracked product of Example 3, so as to respect the ratio of the flow rates of the plant streams. The distillation was repeated under the same conditions as Example 3, with the only difference that the extraction at the head was increased to allow for the increased quantity of hydrocarbons in the feeding. The results, shown in Table 3, show a considerable increase in the concentration of phenol in the stream at the head, thus causing a great increase in the consumption of soda.

EXAMPLE 5

The test of Example 4 was repeated after increasing the reflux ratio. In spite of an increase of about 12% of energy consumption, there was a concentration of phenol in the stream at the head which was basically equal to that of Example 3.

From the data obtained, it can be seen that almost all the phenol (94%) deriving from the extraction (Example 2) is concentrated in the stream at the bottom of the column and is therefore recovered without the necessity of subsequent salification with soda.

EXAMPLE 6 (as a reference)

A solution consisting of water 13.7% w; cumene 13.7% w; α-methylstyrene 3.3% w; phenol 69.3% w was fed at a flow rate of 400 g/hr between plate 30 and 31 of a 60 plate Oldershaw column similar to the one described in Example 3. 123 and 277 g/hr of liquid were removed from the head and bottom respectively.

The operating conditions and results of the test are shown in Table 3.

EXAMPLE 7

The test of Example 6 was repeated after adding to 100 parts by weight of feeding 5.80 parts by weight of the extract of Example 2. The operating conditions were the same as those of the reference test (Example 6) with the only difference that the extraction at the head was increased to allow for the increased quantity of hydrocarbons in the feeding.

The conditions and results of the test are shown in Table 3. In spite of the increase in the concentration of phenol in the stream at the head, about ¾ of the phenol extracted from the aqueous solution was recovered from the bottom of the column and consequently without consumption of soda. Even considering the increase in energy consumed, it can be noted that also with these operating conditions the total economical balance is extremely positive.

EXAMPLE 8 (as a reference)

A solution consisting of water 3.3% w; cumene 15.4% w; α-methylstyrene 3.7% w; phenol 77.6% w was fed at a flow rate of 400 g/hr at plate 26 of a 55 plate Oldershaw column similar to the one described in Example 3. 90 and 310 g/hr of liquid were removed from the head and bottom respectively. The operating conditions and results of the test are shown in Table 3.

EXAMPLE 9

The test of Example 8 was repeated after adding to 100 parts by weight of feeding 6.51 parts by weight of the extract of Example 2. The operating conditions were the same as those of the reference test (Example 8) with the only difference that the extraction at the head was increased to allow for the increased quantity of hydrocarbons in the feeding. The conditions and results of the test are shown in Table 3.

In spite of the increase in the concentration of phenol in the stream at the head, about 62% of the phenol extracted from the aqueous solution was recovered from the bottom of the column and consequently without consumption of soda. Even considering the increase in energy consumed, it can be noted that also with these conditions the total economical balance is extremely positive.

EXAMPLE 10 (as a reference)

In the column of Example 1 the carbon filling was substituted with a filling of ⅜" metal Raschig rings, subdivided into three sections of 3.5 m each. The temperature of the water in the jacket was modified so as to guarantee a test temperature of 50° C.

The following products were fed to this column: at the filling base 10.6 kg/hr of organic stream, coming from the extraction of Example 2, which formed the continuous phase; and at the top 40.92 Kg/hr of an aqueous solution containing sodium phenate and traces of NaOH, also taken from the industrial plant, which formed the dispersed phase. During the passage through the column the phenol contained in the organic phase was completely transferred (99.9%) to the aqueous phase. The composition of the streams fed and of the effluents is shown in Table 4, FIG. 3.

EXAMPLE 11 (as a reference)

The following were fed to the column of Example 10: at the filling base 2.36 Kg/hr of an organic stream, taken from the distillation section for the purification of phenol, having the composition: phenol=60% w; water=1% w; organic impurities=39% w; and at the head 40.92 Kg/hr of the aqueous solution described in Example 10, also taken from the industrial plant. The aqueous phase was dispersed into the organic phase which formed the continuous phase. During the passage through the column the phenol contained in the organic phase was completely transferred to the aqueous phase, as can be seen from the composition of the streams fed and discharged shown in Table 5, FIG. 3.

EXAMPLE 12

The organic phase of the previous example was mixed with the organic phase of the extraction of Example 2 in a ratio of 22.2 parts by weight of the former and 100 parts by weight of the latter. Example 10 was then repeated varying the feeding of the organic phase, which in this test was 12.98 Kg/hr. The flow rate of the aqueous phase was maintained constant at 40.92 Kg/hr. On observing the compositions and flow rates of the streams fed and the effluents, shown in Table 6, FIG. 3, it can be seen that during the test 99.1% of the phenol contained in the organic phase was extracted from the aqueous phase. In particular, on comparing the results obtained in this test with those obtained in the test of Example 11 and with the quantity of phenol present in the sulphatic waters (Example 1), it can be concluded that in this way it is possible to recover 97.1% of the phenol initially contained in the sulphatic waters without the necessity of any additional consumption of NaOH.

TABLE 1

| Components | 1 | | 2 | | 3 | | 4 | |
|---|---|---|---|---|---|---|---|---|
| | g/h | % p | g/h | % p | g/h | % p | g/h | % p |
| $H_2O$ | 54210 | 88.51 | 3 | 0.03 | 54144 | 89.81 | 69 | 0.65 |
| $Na_2SO_4$ | 6130 | 10.01 | | | 6130 | 10.17 | | |
| Phenol | 910 | 1.49 | | | 12 | 0.02 | 898 | 8.46 |
| Organic prod. | | | 9647 | 99.97 | | | 9647 | 90.89 |
| Total | 61250 | 100.00 | 9650 | 100.00 | 60286 | 100.00 | 10614 | 100.00 |

TABLE 2

| | 1 | | 2 | | 3 | | 4 | | 5 | | 6 | |
|---|---|---|---|---|---|---|---|---|---|---|---|---|
| | g/h | % p | g/h | % p | g/h | % p | g/h | % p | g/h | % p | g/h | % p |
| $H_2O$ | 54210 | 88.51 | 3 | 0.03 | 54144 | 89.81 | 3 | 0.03 | 54144 | 89.83 | 69 | 0.65 |
| $Na_2SO_4$ | 6130 | 10.00 | | | 6130 | 10.17 | | | 6130 | 10.17 | | |
| Phenol | 910 | 1.49 | | | 12 | 0.02 | 7 | 0.07 | 5 | <0.01 | 905 | 8.52 |
| Organic | | | 9647 | 99.97 | | | 9647 | 99.90 | | | 9647 | 90.83 |
| Total | 61250 | 100.00 | 9650 | 100.00 | 60286 | 100.00 | 9657 | 100.00 | 60279 | 100.00 | 10621 | 100.00 |

TABLE 3

Experimental conditions and results of the distillation tests for the recovery of phenol

| | ES. 3 | ES. 4 | ES. 5 | ES. 6 | ES. 7 | ES. 8 | ES. 9 |
|---|---|---|---|---|---|---|---|
| Temperature °C. | 90 | 90 | 90 | 90 | 90 | 110 | 105 |
| Head pressure mm Hg | 520 | 520 | 520 | 280 | 280 | 400 | 400 |
| R.R. | 0.314 | 0.315 | 0.518 | 0.98 | 0.98 | 1.63 | 1.63 |
| Head phenol % w | 0.52 | 6.72 | 0.48 | 0.59 | 0.90 | 3.36 | 3.60 |
| Bottom Methylstyr. % w | 0.1 | 0.1 | 0.1 | 0.017 | 0.031 | 0.10 | 0.11 |
| Duty flash K cal/Kg | 95.5 | 94.0 | 94.0 | 65.5 | 68.7 | — | — |
| Duty reboil. K cal/Kg | 72.7 | 81.8 | 86.7 | 110.9 | 109.3 | 100.1 | 112.1 |

TABLE 4

| Components | 1 | | 2 | | 3 | | 4 | |
|---|---|---|---|---|---|---|---|---|
| | g/h | % p | g/h | % p | g/h | % p | g/h | % p |
| NaOH | 41 | 0.10 | | | | | | |
| Phenate | 4090 | 10.00 | | | 4209 | 10.05 | | |
| $H_2O$ | 36789 | 89.90 | 69 | 0.65 | 36866 | 88.02 | 10 | 0.10 |
| Phenol | | | 905 | 8.52 | 809 | 1.93 | <1 | <0.01 |
| Organic prod. | | | 9647 | 90.83 | | | 9647 | 99.90 |
| Total | 40920 | 100.00 | 10621 | 100.00 | 41884 | 100.00 | 9657 | 100.00 |

TABLE 5

| Components | 1 g/h | 1 % p | 2 g/h | 2 % p | 3 g/h | 3 % p | 4 g/h | 4 % p |
|---|---|---|---|---|---|---|---|---|
| NaOH | 41 | 0.10 | | | | | | |
| Phenate | 4090 | 10.00 | | | 4209 | 9.94 | | |
| $H_2O$ | 36789 | 89.90 | 24 | 1.00 | 36831 | 86.94 | | |
| Phenol | | | 1416 | 60.00 | 1320 | 3.12 | | |
| Organic prod. | | | 920 | 39.00 | | | 920 | 100.00 |
| Total | 40920 | 100.00 | 2360 | 100.00 | 42360 | 100.00 | 920 | 100.00 |

TABLE 6

| Components | 1 g/h | 1 % p | 2 g/h | 2 % p | 3 g/h | 3 % p | 4 g/h | 4 % p |
|---|---|---|---|---|---|---|---|---|
| NaOH | 41 | 0.10 | | | | | | |
| Phenate | 4090 | 10.00 | | | 4209 | 9.72 | | |
| $H_2O$ | 36789 | 89.90 | 93 | 0.72 | 36889 | 85.19 | 11 | 0.10 |
| Phenol | | | 2321 | 17.88 | 2204 | 5.09 | 21 | 0.20 |
| Organic prod. | | | 10567 | 81.40 | | | 10567 | 99.70 |
| Total | 40920 | 100.00 | 12981 | 100.00 | 43302 | 100.00 | 10599 | 100.00 |

We claim:

1. A process for the recovery of phenol dissolved in an aqueous sulphatic stream discharged from a reactor in which cumene hydroperoxide is cleaved to phenol and acetone, comprising:

extracting phenol present in said aqueous sulphatic stream containing phenol, $Na_2SO_4$ and organic impurities in a multi-stage extractor with an organic solvent, thereby forming an extracted product organic phase and a refined aqueous product phase, the ratio of the extracted product organic phase to the refined aqueous product phase consists essentially of 0.1 to 1 v/v at a temperature ranging from 20°–70° C.; and obtaining phenol by distillation or re-extraction of the recovered extracted product organic phase.

2. The process of claim 1, wherein the ratio of extracted product organic phase to refined product aqueous phase ranges from 0.15 to 0.25 v/v.

3. The process of claim 1, wherein the temperature of extraction ranges from 25° to 60° C.

4. The process of claim 1, wherein said organic solvent for the extraction of phenol from the aqueous sulphatic stream comprises cumene, α-methylstyrene and acetone.

5. The process of claim 1, wherein the refined aqueous product discharged from the multi-stage extractor is equicurrently extracted with solvent before the solvent is fed to the multi-stage extractor.

6. The process of claim 1, wherein said phenol is recovered by distillation.

7. The process of claim 6, wherein said distillation occurs by primary distillation.

8. The process of claim 1, wherein phenol is recovered by re-extraction from the organic phase in a multi-stage extractor with an aqueous solution of sodium phenate as solvent.

9. The process of claim 8, wherein the organic phase is mixed with another organic stream containing phenol, before re-extraction with the aqueous sodium phenate solution.

* * * * *